United States Patent [19]

Traverso et al.

[11] Patent Number: 5,202,041
[45] Date of Patent: Apr. 13, 1993

[54] SKI LUBRICANT COMPRISING PARAFFINIC WAX AND A HYDROCARBON COMPOUND CONTAINING A PERFLUORO SEGMENT

[75] Inventors: Enrico Traverso, Monza; Antonio Rinaldi, San Donato Milanese, both of Italy

[73] Assignee: Enichem Synthesis S.p.A., Palermo, Italy

[21] Appl. No.: 663,417

[22] Filed: Mar. 1, 1991

[30] Foreign Application Priority Data

Mar. 2, 1990 [IT] Italy .................. 19537 A/90

[51] Int. Cl.$^5$ ............... C10M 139/00; C10M 111/04; A63C 5/00
[52] U.S. Cl. ........................ 252/58; 280/610
[58] Field of Search .................... 252/58; 280/610

[56] References Cited

U.S. PATENT DOCUMENTS

| | | | |
|---|---|---|---|
| 2,411,159 | 11/1946 | Hanford | 252/58 |
| 2,562,547 | 7/1951 | Hanford et al. | 252/58 |
| 3,067,262 | 12/1962 | Brady | 252/58 |
| 3,069,280 | 12/1962 | Spiegler | 252/58 |
| 3,145,222 | 8/1964 | Brace | 252/58 |
| 4,724,093 | 2/1988 | Gambaretto | 252/58 |
| 5,069,976 | 12/1991 | Vuachet et al. | 280/610 |
| 5,131,674 | 7/1992 | Tokui et al. | 252/25 |

FOREIGN PATENT DOCUMENTS

0132879 2/1985 European Pat. Off. .
3816467 12/1988 Fed. Rep. of Germany .
2573662 5/1986 France .

OTHER PUBLICATIONS

Tweig, R. et al., Chemical Abstracts, vol. 101, No. 2 (Jul. 9, 1984) "Synthesis and Characterization of Perfluoroalkyl-alkanes as models for Semi-Flexible Polymers"-No. 7909r.

Primary Examiner—Jerry Johnson
Attorney, Agent, or Firm—Shea & Gould

[57] ABSTRACT

Compounds which can be defined by the formula (I):

$$CF_3-C_nF_{2n}-C_mH_{2m}-CH_3 \qquad (I)$$

wherein:
n is a numeral comprised within the range of from 1 to 21;
m is a numeral comprised within the range of from 3 to 25;
n+m is a numeral equal to, or higher than, 18;
with the chain of carbon atoms being either linear or branched are used as agents affording sliding characteristics (ski-waxes) for skis, to be applied onto the ski sole, and/or to be incorporated inside the ski sole. A sliding composition is also disclosed, which contains a paraffinic wax and at least one compound with formula (I).

7 Claims, No Drawings

SKI LUBRICANT COMPRISING PARAFFINIC WAX AND A HYDROCARBON COMPOUND CONTAINING A PERFLUORO SEGMENT

The present invention relates to agents affording sliding characteristics and to their use to afford sliding characteristics to skis.

In the art the use is known of ski-waxes to improve the sliding characteristics of skis. These ski-waxes normally contain such substances as animal oils, vegetable oils, paraffinic waxes, fatty alcohols, esters of fatty alcohols and still other chemicals, usually as more or less complex mixtures.

In the art, also agents of non-traditional type to afford sliding characteristics to skis have been disclosed, which agents are endowed with improved characteristics compared to conventional ski-waxes. In particular, European Patent Application Publication No. 132,879 discloses a solid agent for affording sliding characteristics to skis, which is essentially constituted by linear perfluoroparaffins containing from 10 to 20 carbon atoms in their molecule, which can be used also as mixtures with paraffinic waxes and in general with conventional ski-waxes. The drawback which affects these sliding agents basically consists in their poor compatibility with paraffinic waxes, so that in general a compatibilizer agent must be used, in particular a fluorinated surfactant.

The present Applicant has found now that some organic compounds consisting of a paraffinic hydrocarbonaceous segment and a perfluorinated paraffinic hydrocarbonaceous segment chemically linked to each other, constituted extremely good sliding agents for skis. In particular, the present Applicant was able to find that a such a sliding effect manifests itself both whether the compounds are applied to the ski sole, or if they are incorporated inside said ski sole, during a step of the ski manufacturing process. The present Applicant has also found that these compounds consisting of two segments are compatible with the conventional ski-waxes and that they can be mixed with the latter without the aid of any compatibilizer agents, to yield composition which make it possible improved performances to be obtained in the ski sector.

In accordance therewith, according to an aspect thereof, the present invention relates to a compound or mixture of compounds with formula (I):

wherein:
$n$ is a numeral comprised within the range of from 1 to 21;
$m$ is a numeral comprised within the range of from 3 to 25;
$n+m$ is a numeral equal to, or higher than, 18;
with the chain of carbon atoms being an either linear or branched chain;
to be used as an agent to afford sliding characteristics (i.e., as a ski-wax) to skis.

According to a preferred form of practical embodiment of the present invention in formula (I):
$n$ is a numeral comprised within the range of from 3 to 15;
$m$ is a numeral comprised within the range of from 5 to 23;
and
$n+m$ is a numeral equal to or higher than 18;
with the chain of carbon atoms being an either linear or substantially linear chain.

According to the present invention by "linear or substantially linear" with regard to the chains of carbon atoms of compounds with formula (I), it is herein meant that said chains are linear for at least 90%, up to 100%.

Examples of specific compounds with formula (I) are:
CF3—(CF2)5—(CH2)15—CH3—a semi-solid, colourless product with waxy appearance, with melting point 31°-32° C.;
CF3—(CF2)7—(CH2)15—CH3—a solid, colourless product with waxy appearance, with melting point 49°-51° C.;
CF3—(CF2)7—(CH2)19-13 CH3—a solid, colourless product with waxy appearance, with melting point 68°-72° C.;
CF3—(CF2)7—(CH2)p—CH3—a solid, colourless product with waxy appearance, which is a mixture of four components with p=17, 19, 21 and 23, with melting point 59°-62° C.

The compounds with formula (I) can be prepared by methods known in the art and disclosed, e.g., in U.S. Pat. No. 3,145,222 and J. Org. Chem. 34, 2441 (1969) and 40, 851 (1975).

The preferred process to prepare the compounds with formula (I) comprises:

(a) a reaction of addition of a 1-perfluoroalkyl iodide and an alpha-olefin, in the presence of a free-radical catalyst, according to the following reaction scheme:

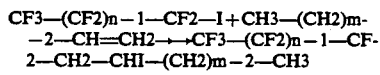

(b) a reaction of reduction of the product of reaction from the (a) step, carried out with zinc powder in the presence of aqueous hydrochloric acid, according to the following reaction scheme:

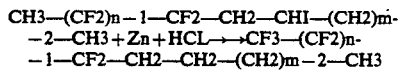

More particularly, the addition reaction (a) is carried out in the absence of solvents or diluents, with an excess of at least 50% of either of the reactants. The free-radical catalyst is a catalyst capable of forming free radicals under the conditions under which the reaction is carried out.

For that purpose, azo-compounds are advantageously used, such as azo-bis-isobutyronitrile, or peroxides, such as benzoyl peroxide and 3-tert.butyl-peroxyethylhexanoate. The reaction temperature is generally comprised within the range of from 60° to 100° C., and is anyway selected as a function of the particular free-radical initiator and of the relevant decomposition kinetics. At reaction end, the excess of reactant is removed by evaporation under reduced pressure. By operating under the above conditions, yields and selectivities to the useful reaction product higher than about 95% are usually accomplished.

In the step (b), the reduction reaction is carried out by adding to the reaction mixture coming from the (a) step, a solvent and generally a low-boiling aliphatic alcohol (e.g. ethanol), zinc powder and then aqueous hydrochloric acid, for example hydrochloric acid at a concentration comprised within the range of from 10 to 37% by weight. Zinc and hydrochloric acid are added in an excess of at least 100% relatively to the stoichiometric amount required for the reduction. Under these conditions, the yield of the reduction reaction is higher than approximately 99%. At the end of the reaction, the reaction mixture is diluted with a solvent (e.g., toluene) and water, so as to allow a good separation of the aqueous and organic phases to take place. The reaction mixture should advantageously be kept at temperatures higher than room temperatures, so as to prevent the reaction product contained in the organic phase from solidifying. The excess of zinc is filtered off. The organic phase is separated from the aqueous phase, the solvent is evaporated off under reduced pressure and the desired reaction products is recovered.

According to the present invention, the compounds or mixtures of compounds (I) are used as agents affording sliding characteristics (ski-waxes) to skis, by application onto the ski sole, in particular a polyethylene sole. For example, the application may be carried out by melting the compounds (I) on the spot with a hot iron, followed by a leveling by means of a blade and brushing. The function of so applied compounds (I) is of reducing to a considerable extent the surface tension of the ski sole, increasing the water-repellancy thereof, and allowing skis to slide more easily on the water film which is formed, due to pressure and friction phenomena, at the interface between the their sole and the underlying snow.

According to another form of practical embodiment of the present invention, the compounds (I) are incorporated inside the ski sole. Ski soles are normally made from high-density polyethylene, They tipically show a thickness of from 1.2 to 1.4 mm and are manufactured by processes of polymer extrusion or of polymer powder sintering. In case of extrusion, a polyethylene is normally used which has an average molecular weight of the order of 400,000–800,000, and the extrusion is carried out at temperatures of the order of from 220° to 240° C. A polyethylene useful for that purpose is the product available from BASF company under the trade name "Lupolen 5661B". The so manufactured ski soles are normally intended for use on the skis for non-competitive sector. In case of manufacture by sintering, a polyethylene having a high average molecular weight (of the order of from 3 to 5 millions) is used. A polyethylene useful for that purpose is the product available from Hoechst company as "Hostalen-Gur-412". The process consists in sintering the polymer powder at temperatures of from 250° to 300° C., under pressures of from 150 to 200 kg/cm$^2$, for times of the order of from 12 to 24 hours, inside moulds with cylindrical shape, whose height equates the width of the ski sole. The resulting polyethylene cylinder is laminated along its circumference. The so manufactured ski soles are intended for use in the competitive sector. In order to accomplish an improvement in the sliding characteristics of the so obtained ski soles, the compounds (I), and in particular those with a higher molecular weight, non-volatile or at least poorly volatile under processing conditions, are mixed with the polymer powder and the so obtained mixture is submitted to the extrusion or sintering treatments as disclosed above. In particular, the amount of compounds (I) admixed with the polymer powder may be comprised within the range of from 0.5 to 10% by weight, and preferably of from 2 to 8% by weight, relatively to the weight of the sole. The so obtained soles show a decrease in their surface tension, evidenced by a significant increase in the contact angle, compared to the soles manufactured from the same polyethylene in the absence of the compounds of formula (I). This decrease in surface tension is thought to derive from the fact that the perfluorinated chain of the compounds (I) tend to position itself towards the outside on the limit surface, orientating itself, in such a way as to generate a "brush effect".

Of source, the application of compounds (I) inside the sole and onto the sole of a same ski falls within the scope of the present invention.

Therefore, according to another aspect thereof, the present invention relates to a ski characterized in that it bears on its sole and/or incorporated inside its sole, at least one compound of formula (I).

According to yet another aspect, the present invention relates to a composition (mixture) affording sliding characteristics, which comprises:
a paraffinic wax, and
a compound or mixture of compounds with formula (I), as defined above.

By the term "paraffinic wax" according to the present invention those products known from the prior art are meant which are usually spread on the ski sole in order to increase the sliding characteristics thereof and which, besides to waxes or paraffinic compounds in general, may contain one or more from animal or vegetable oils, fatty alcohols and esters of fatty alcohols, fatty acids and esters, fatty acids amides and salts, or any other ingredients conventionally used for that purpose, such as, e.g., siliconic compounds, Teflon powder and graphite powder. In particular, within the scope of this definition the conventional ski-waxes fall, which incorporate one or more of the above reported compounds, and which are easily available on the market.

In the composition affording sliding characteristics according to the present invention, the content of compound or mixture of compounds with formula (I) may be generally comprised within the range of from 0.1 to 99% by weight and preferably of from 3 to 25% by weight, relatively to the weight of the composition.

In particular, the present Applicant was able to find that the compounds of formula (I) can be mixed and homogenized with a paraffinic wax, or normally with a conventional ski-wax available from the market, by melting the ingredients, with no need to use compatibilizer agents. The mixture and homogenizing of compounds of formula (I) into a paraffinic wax or into a conventional ski-wax can be obtained as well by dissolving at high temperature the ingredients in a suitable solvent, for example white spirit, or in an aliphatic solvent based on octane or decane, followed by partial or total co-precipitation at low temperature of the solid ingredients in dispersed form. In this case a more or less thick paste is obtained which is easily applied to the ski sole, for example by a cloth. The treatment with the leveling blade and the brushing are carried out after the evaporation of the solvent. In any case the non-fluorinated paraffinic portion of compounds (I) allows the dissolving effect into the commercial ski-waxes, which generally show a high affinity for such a paraffinic portion, to take place. Furthermore, when such a composition or mixture is applied to the sole of a ski, the fluorinated paraffinic portion of compounds (I) tends to position itself at the limit surface, with a "brush effect", lowering the surface tension thereof, as demonstrated by significant increase in contact angle, as compared to conventional ski-waxes.

Therefore, the introduction of the compounds of formula (I) into the conventional ski-waxes enhances the sliding effect thereof. Such an improvement can be observed under all conditions of snow temperature and air humidity, and is optimum with snow temperatures comprised within the range of from 0° to −15° C., and with a relative humidity of atmospheric air comprised within the range of from 40 to 100%. The extent of such improvements, evaluated on snow-covered fields, on stretches with a length of the order of 150 meters and with slopes of the order of 20%, is such as to allow a reduction of up to about 3% in descent time to be accomplished.

Therefore, according to a further aspect thereof, the present invention relates to a ski characterized in that it bears on its sole the sliding composition as defined above, and which may additionally contain at least one compound of formula (I) incorporated inside its sole.

The following experimental examples are reported to better illustrate the present invention.

EXAMPLE 1

Preparation of $CF_3$—$(CF_2)_7$—$(CH_2)_{19}$—$CH_3$ (Molecular weight 700).

The following are charged to a three-necked flask of two liters of capacity equipped with stirrer and bubble condenser, heated in an oil bath:
- 920 g of n-1-perfluorooctyl iodide (molecular weight 546; 1.68 mol); and
- 246 g of n-alpha-eicosene (molecular weight 280; 0.878 mol).

After heating up to 85° C.,
- 3 g of tert.-butyl-peroxy-ethyl-hexanoate is added, with good stirring, as three portions of 1 g each at intervals of one hour.

The reaction of addition of n-1-perfluorooctyl iodide to the double bond of n-alpha-eicosene is exothermic (maximum increase in temperature about 15° C.). The reaction mixture is kept at a temperature comprised within the range of from 85° to 100° C. for a total time of six hours. At the end of this time period, 0.6% of the initial amount of n-alpha-eicosene is still present (determination by gas-chromatography). The excess of perfluoro-alkyl iodide is evaporated off by heating the reaction mixture up to 115° C. and decreasing the pressure down to 5 mm Hg.

The reaction mixture is then cooled down to 60° C. and the following are added:
- 320 ml of ethanol; and
- 200 g of zinc powder (70–100 μm).

Subsequently,
- 200 ml of hydrochloric acid at 37% (weight/weight) is added in an 80-minutes time and with strong stirring.

The reduction reaction is an exothermic one and the temperature increases up to 78°–80° C., the boiling point of ethanol-water azeotropic mixture. One hour later than the end of the addition of hydrochloric acid, the reaction is complete and no organic iodide is present any longer (gas-chromatographic determination).

With temperature being maintained at about 70° C.,
- 400 ml of hot toluene; and
- 200 ml of hot water are added.

The mixture is filtered when hot in order to remove any unreacted zinc. The lower aqueous phase is separated from the filtrate and is discarded. The organic phase is recovered. The latter is washed three times, at high temperature, with an aqueous solution containing 5–10% by weight of sodium chloride and 1% by weight of sodium carbonate. The solvent is completely removed from the organic phase by distillation under vacuum (temperature up to 130° C.; pressure up to 5 mm Hg).

The distillation residue is cooled and 600 grams is obtained of a nearly colourless mass, a waxy solid with a melting point of 68°–72° C., containing 0.3% by weight of olefin (gas-cromatographic analysis) and with an iodine content of 345 ppm (parts per million parts by weight).

NMR ANALYSIS $CH_3$—$CH_2$—$(CH_2)$—$CH_2$—$CH_2$—$R_F$ paraffinic chain; solvent $CDCl_3$; reference tetramethyl silane.

$CH_3$: 0.861 ppm; multiplet; 1 C atom;
$CH_2$—: 1.240 ppm; multiplet; 17 C atoms;
$CH_2$—: 1.577 ppm; multiplet; 1 C atom;
$CH_2$: 2.027 ppm; multiplet; 1 C atom;

$CF_3$—$CF_2$—$CF_2$—$(CF_2)_3$—$CF_2$—$CF_2$—$RH$ perfluorinated chain, solvent $CDCl_3$; reference $CFCl_3$.

$CF_3$: −82.16 ppm; singlet; 1 C atom;
$CF_2$—: −115.60 ppm; singlet; 1 C atom;
$CF_2$—: −123.26 ppm; singlet; 3 C atoms;
$CF_2$—: −124.10 ppm; singlet; 1 C atom;
$CF_2$—: −124.90 ppm; singlet; 1 C atom;
$CF_2$—: −127.52 ppm; singlet; 1 C atom.

In the following Examples 2, 3 and 4, further compounds with formula (I) according to the present invention are prepared. The method used is the same as of Example 1 and for each example the data is reported as indicated hereunder.

For the addition reaction:
n-1-perfluoro-alkyl iodide: type and amount,
n-alpha-olefin: type and amount,
catalyst: type and amount,
temperature and reaction time;
For the reduction reaction:
zinc powder: amount,
hydrochloric acid at 37% by weight: amount.
End product: amount and characteristics.

EXAMPLE 2

Preparation of $CF_3$—$(CF_2)_7$—$CH_2$—$CH_2$—$(CH_2)_p$—$CH_3$ (average molecular weight 715; mixture of components with p=15, 17, 19 and 21).

Addition reaction:
n-1-perfluorooctyl iodide: 950 g; 1.74 mol;
n-alpha-olefin: $CH_2$=$CH$—$(CH_2)_p$—$CH_3$: 240 g; 0.82 mol; mixture of:

| | |
|---|---|
| n-alpha-octadecene | 1% by weight |
| n-alpha-eicosene | 49% by weight |
| n-alpha-docosene | 42% by weight |
| n-alpha-tetracosene | 8% by weight | tert.-butyl-peroxy-ethylhexanoate: 3 g;
85° C.; 8 hours.
Reduction reaction:
zinc powder: 200 g;
hydrochloric acid at 37% by weight: 220 ml.
End product:
550 g is obtained of a solid waxy mass, slightly yellow coloured, with melting temperature 59°–62° C., which contains 1.5% by weight of olefins, with its composition being reacher of higher molecular weight components.

EXAMPLE 3

Preparation of CF3—(CF2)7—CH2—CH2—(CH2)-13—CH3 (molecular weight 644).
Addition reaction:
n-1-perfluorooctyl iodide: 273 g; 0.5 mol;
n-alpha-hexadecene: 68 g; 0.3 mol;
azo-bis-isobutyronitrile: 0.8 g;
75°-80° C.; 5 hours.
Reduction reaction:
zinc powder: 60 g;
hydrochloric acid at 37% by weight: 100 ml.
End product:
180 g is obtained of a solid waxy mass, which is colourless, has a melting temperature of 49°-51° C., and contains 0.2% by weight of olefins.

EXAMPLE 4

Preparation of CF3—(CF2)5—CH2—CH2—(CH2)-13—CH3 (molecular weight 544).
Addition reaction:
n-1-perfluorohexyl iodide: 300 g; 0.67 mol;
n-alpha-hexadecene: 90 g; 0.4 mol;
azo-bis-isobutyronitrile: 0.8 g;
75°-80° C.; 5 hours.
Reduction reaction:
zinc powder: 80 g;
hydrochloric acid at 37% by weight: 100 ml.
End product:
210 g of a semisolid, colourless, waxy mass with melting temperature 31°-32° C., which contains 0.12% by weight of olefin, is obtained.

EXAMPLE 5

The evaluation of the product is carried out by two ski masters, specialized in carrying out tests. Each of them has available two pairs of ski for ski competitions, perfectly equal, known under the trade name "ATOMIC". In each one of said two ski pairs, the soles of one ski pair are treated with the ski-wax "Holmenkol" SPACE-GLIDER GRAPHIT SG, available from the market, and the soles of the other pair of skis are treated with the same ski-wax, to which 15% by weight, with reference to the total weight of the mixture, of the product of Example 1 is added.
Environmental characteristics:
old snow of winter type, beaten with a mechanical means and then with 20 high-speed skier passages; thickness of snowcoat higher than 50 cm;
air temperature: from 0° to −2° C.;
snow temperature: from −4° to −6° C.;
relative humidity of snow surface: 78-80%.
All the descents and measurements are performed in the absence of sun.
Characteristics of the ski-run:
The ski-run is situated at the level of 1850 m above the sea-level, is perfectly straight, is 155 m long and shows a vertical height of approximately 50 m.
Before entering the ski-run, the skiers run along a high-slope launching stretch, 98 m long.
Examples of descent
Each skier runs along the ski-run three times, with each of his two pairs of skis. The average time of descent is as follows:
with Holmenkol ski-wax: 7.54 seconds (t1) (average value from six tests);
with Holmenkol ski-wax containing 15% by weight of product of Example 1: 7.38 seconds (t2) (average value from six tests).

$$\Delta t\% = (t1 - t2)/t1 \times 100 = 1.59\%$$

The evaluation is repeated the day after. The ski soles are carefully cleaned with the cleaning agent "Toko" currently available from the market. Both said ski pairs treated the day before with the sky-wax available from the market are treated with the ski-wax admixed with the product from Example 1, as indicated above, and the contrary is done on the other two pairs of skis.
In this case, the temperature of snow is comprised within the range of from −6° to −8° C. and air temperature is comprised within the range of from −3° to −4° C., with a relative humidity of snow surface of 68-72%. Results are obtained, which are at all similar to as reported above.

EXAMPLE 6

This test is carried out in the same way as in above Example 5, using the following ski-waxes:
ski-wax available from the market "Briko yellow grade" (of universal type); and
ski-wax available from the market "Briko yellow grade" (of universal type) admixed with 20% by weight (relatively to the total weight of the mixture) of the product of Example 2.
The tests are carried out under the following conditions:
air temperature: from +1° to 0° C.;
snow temperature: from −2° to −4° C.;
relative surface humidity: 80-83%.
The following descent times are measured:
with "Briko yellow grade" ski-wax: 7.49 seconds (t1) (average value from six tests);
with "Briko yellow grade" ski-wax containing 20% by weight of the product of Example 1: 728 seconds (t2) (average value from six tests);

$$\Delta t\% = (t1 - t2)/t1 \times 100 = 2.8\%.$$

EXAMPLE 7

The instant example is carried out similarly to Example 5, with two appraisers, specialized ski masters, each having two racing ski pairs.
The characteristics of snow are: old snow, of spring type, leveled but not very much beaten. Before the test several high-speed passages are carried out. The ski-run is perfectly straight, is 120 m long, with a high initial slope and nearly horizontal in the end portion. The launching stretch, with high slope, is 40 meters long.
The other conditions are:
air temperature: from −8° to −10° C.;
snow temperature: from −9° to −11° C.;
relative surface humidity: 71-73%.
The descents are carried out in the absence of sun.
A ski-wax available from the market "Swix violet" and a mixture of the latter with 10% by weight (with reference to the weight of the mixture) of the product of Example 1 are used.
The following descent times are measured:
with "Swix violet" ski-wax: 5.97 seconds (t1) (average value from ten tests);
with "Swix violet" ski-wax containing 10% by weight of product from Example 1: 5.93 seconds (t2) (average value from 10 tests).

$$\Delta t\% = (t1 - t2)/t1 \times 100 = 0.67\%.$$

EXAMPLE 8

400 g of the product of Example 1, as microgranules with average size 0.4-0.5 mm, is mixed, in a planetary mixer, with 10 kg of high-density polyethylene powder, a product marketed under the trade name "Lupolen" 5661B (BASF).

The mixture if extruded with a screw extruder with laminar head, at 220° C. A band of 10 cm of width and 1.5 mm of thickness is obtained.

A portion of this band is polished with abrasive paper and then is kept at 60° C. in an oven for 48 hours.

ESCA analysis (Electron Spectroscopy for Chemical Analysis) of the surface, down to a depth of about 0.2 $\mu$m, shows the presence of fluorine in a concentration of 5.3% by weight. The contact angle of the same surface is of 111°.

A band of "Lupolen" 5661B in its pristine state, not admixed with the product of Example 1, prepared and treated by the same methodology, shows a contact angle of 73°.

We claim:

1. Composition affording sliding characteristics, which comprises:
   a paraffinic wax, and
   a compound or mixture of compounds with formula (I):

$$CF_3-C_nF_{2n}-C_m-H_{2m}-CH_3 \quad (I)$$

wherein:
   n is a numeral comprised within the range of from 1 to 21;
   m is a numeral comprised within the range of from 3 to 25;
   n+m is a numeral equal to, or higher than, 18;
   with the chain of carbon atoms being either linear or branched.

2. Composition affording sliding characteristics according to claim 1, in which in said formula (I):
   n is a numeral comprised within the range of from 3 to 15;
   m is a numeral comprised within the range of from 5 to 23;
   n+m is a numeral equal to, or higher than, 18;
   with the chain of carbon atoms being either linear or substantially linear.

3. Composition affording sliding characteristics according to claim 2, in which said compounds with formula (I) are:
   $CF_3-(CF_2)15-(CH_2)15-CH_3$—a semi-solid, colourless product with waxy appearance, with melting point 31°-32° C.;
   $CF_3-(CF_2)7-(CH_2)15-CH_3$—a solid, colourless product with waxy appearance, with melting point 49°-51° C.;
   $CF_3-(CF_2)7-(CH_2)19-13\ CH_3$—a solid, colourless product with waxy appearance, with melting point 68°-72° C.;
   $CF_3-(CF_2)7-(CH_2)p-CH_3$—a solid, colourless product with waxy appearance, which is a mixture of four components with p=17, 19, 21 and 23, with melting point 59°-62° C.

4. Composition affording sliding characteristics according to claim 3, in which the content of compound or mixture of compounds with formula (I) is comprised within the range of from 0.1 to 99% by weight, relatively to the weight of the composition.

5. Composition affording sliding characteristics according to claim 4, in which said content of compound or mixture of compounds with formula (I) is comprised within the range of from 3 to 25% by weight, relatively to the weight of the composition.

6. Process for endowing a ski with sliding characteristics, in which a composition as defined in claim 1 is applied onto the sole of said ski and/or is incorporated inside the sole of said ski.

7. Process for endowing a ski with sliding characteristics, in which a composition as defined in claim 5 is applied onto the sole of said ski and/or is incorporated inside the sole of said ski.

* * * * *